United States Patent
Bram

(10) Patent No.: US 12,220,296 B1
(45) Date of Patent: Feb. 11, 2025

(54) OSTEOTOMY DRILL BIT TO PRODUCE AN OPTIMALLY SHAPED JAWBONE OPENING FOR A DENTAL IMPLANT AND ABUTMENT

(71) Applicant: Gary Bram, Woodbury, NY (US)

(72) Inventor: Gary Bram, Woodbury, NY (US)

( * ) Notice: Subject to any disclaimer, the term of this patent is extended or adjusted under 35 U.S.C. 154(b) by 1091 days.

(21) Appl. No.: 16/998,253

(22) Filed: Aug. 20, 2020

Related U.S. Application Data

(63) Continuation-in-part of application No. 16/704,286, filed on Dec. 5, 2019, now Pat. No. 11,471,172.

(60) Provisional application No. 62/776,246, filed on Dec. 6, 2018.

(51) Int. Cl.
   *A61C 8/00* (2006.01)
   *A61B 17/16* (2006.01)
   *A61C 3/02* (2006.01)

(52) U.S. Cl.
   CPC ........ *A61C 8/0089* (2013.01); *A61B 17/1615* (2013.01); *A61B 17/1673* (2013.01); *A61C 3/02* (2013.01)

(58) Field of Classification Search
   CPC ........... A61C 8/0089; A61C 3/02; A61C 3/00; A61B 17/1615; A61B 17/1673; A61B 17/1613; A61B 17/16; A61B 17/1662
   USPC ....................................................... 433/164
   See application file for complete search history.

(56) References Cited

U.S. PATENT DOCUMENTS

| | | | |
|---|---|---|---|
| 137,434 A | 4/1873 | Gillespie | |
| 362,934 A | 5/1887 | Champion | |
| 716,441 A | 12/1902 | Latham | |
| 1,216,683 A | 2/1917 | Greenfield | |
| 1,333,388 A | 3/1920 | Chester | |
| 1,643,679 A | 9/1927 | Roderick | |
| 2,264,922 A | 12/1941 | Hooser | |

(Continued)

FOREIGN PATENT DOCUMENTS

| | | |
|---|---|---|
| JP | H06125923 A | 5/1994 |
| KR | 101166161 B1 | 7/2012 |

(Continued)

OTHER PUBLICATIONS

Kai Guo, Based On Logistic Curve Have An S-shaped Blade-breaking Drill, CN 106077767 B—with machine translation (Year: 2018).*

*Primary Examiner* — Ralph A Lewis
*Assistant Examiner* — Mirayda A Aponte
(74) *Attorney, Agent, or Firm* — Thomas O'Rourke; James Bongiorno; O'ROURKE IP LAW PLC

(57) ABSTRACT

A dental drill bit for creating a particularly shaped osteotomy in a human jawbone includes: a mounting shank and cutting head. The cutting head includes: four blades protruding away from an axis of the drill bit, each blade having a thickness and being positioned 90 degrees to each adjacent blade to form a cruciform-shaped cross-section, with two pairs of the blades each positioned 180 degrees apart. Each of the pair of blades positioned 180 degrees apart are offset laterally a distance about equal to the blade thickness, and each blade has a shaped periphery that includes: a first radiused periphery; and a second radiused periphery. The first radiused periphery is shaped to form a hemisphere frustum-shaped socket portion when rotated about the axis of the drill bit, and the second radiused periphery is shaped to form a bullet shaped socket portion when rotated about the axis of the drill bit.

7 Claims, 14 Drawing Sheets

(56) References Cited

U.S. PATENT DOCUMENTS

| | | |
|---|---|---|
| 3,461,875 A | 8/1969 | Hall |
| 3,564,945 A | 2/1971 | Bradley |
| 3,824,027 A | 7/1974 | Janci |
| 4,021,920 A | 5/1977 | Kirschner |
| 4,190,958 A | 3/1980 | Martin |
| 4,273,117 A | 6/1981 | Neuhauser |
| 4,325,153 A | 4/1982 | Finnegan |
| 4,341,206 A | 7/1982 | Perrett |
| 4,345,899 A | 8/1982 | Vlock |
| 4,504,519 A | 3/1985 | Zelez |
| 4,507,028 A | 3/1985 | Matsushita |
| 4,561,812 A | 12/1985 | Linden |
| 4,681,541 A | 7/1987 | Snaper |
| 4,738,616 A | 4/1988 | Reynaud |
| 4,787,848 A | 11/1988 | Ross |
| 4,936,721 A | 6/1990 | Meyer |
| 4,951,690 A | 8/1990 | Baker |
| 4,957,397 A | 9/1990 | Huff |
| 4,990,088 A | 2/1991 | Weissman |
| 5,051,092 A | 9/1991 | Miller |
| 5,098,293 A | 3/1992 | Loof |
| 5,098,737 A | 3/1992 | Collins |
| 5,100,322 A | 3/1992 | Weissman |
| 5,261,818 A | 11/1993 | Shaw |
| 5,299,937 A | 4/1994 | Gow |
| 5,429,504 A | 7/1995 | Peltier |
| 5,569,035 A | 10/1996 | Balfour |
| 5,573,537 A | 11/1996 | Rogozinski |
| 5,575,650 A | 11/1996 | Niznick |
| 5,653,812 A | 8/1997 | Petrmichl |
| 5,681,653 A | 10/1997 | Hammond |
| 5,762,498 A | 6/1998 | Gonzalez |
| 5,763,087 A | 6/1998 | Falabella |
| 5,766,394 A | 6/1998 | Anderson |
| 5,772,760 A | 6/1998 | Gruen |
| 5,791,902 A | 8/1998 | Lauks |
| 5,799,549 A | 9/1998 | Decker |
| 5,816,807 A | 10/1998 | Matsutani |
| 5,868,572 A | 2/1999 | Lazzaro |
| 5,941,706 A | 8/1999 | Ura |
| 6,146,138 A | 11/2000 | Dalmau |
| 6,179,615 B1 | 1/2001 | Blacklock |
| 6,312,432 B1 | 11/2001 | Leppelmeier |
| 6,364,662 B1 | 4/2002 | Kumar |
| 6,419,490 B1 | 7/2002 | Kitchings Weathers, Jr. |
| 6,641,395 B2 | 11/2003 | Kumar |
| RE38,630 E | 10/2004 | Lazzara |
| 6,863,529 B2 | 3/2005 | Strong |
| 8,770,974 B2 | 7/2014 | Suter |
| D741,484 S | 10/2015 | Cho |
| 10,543,059 B2 | 1/2020 | Shiori |
| D898,915 S | 10/2020 | Chen |
| 2002/0031745 A1 | 3/2002 | Kumar |
| 2003/0022132 A1 | 1/2003 | Jesch |
| 2006/0210949 A1 | 9/2006 | Stoop |
| 2007/0065777 A1 | 3/2007 | Becker |
| 2008/0085488 A1 | 4/2008 | Lazarof |
| 2009/0080989 A1 | 3/2009 | Dost |
| 2009/0239200 A1 | 9/2009 | Brajnovic |
| 2009/0274996 A1* | 11/2009 | Miller .................... A61C 1/084 433/165 |
| 2009/0305189 A1 | 12/2009 | Scortecci |
| 2010/0112517 A1 | 5/2010 | Chen |
| 2012/0330315 A1 | 12/2012 | Ranck |
| 2013/0004253 A1 | 1/2013 | Kauper |
| 2013/0218160 A1* | 8/2013 | Bjorn ................. A61B 17/1695 606/80 |
| 2014/0127640 A1 | 5/2014 | Zacharia |

FOREIGN PATENT DOCUMENTS

| | | |
|---|---|---|
| KR | 200467202 Y1 | 6/2013 |
| KR | 20190035012 A | 4/2019 |
| KR | 20190116604 A | 10/2019 |
| WO | WO1990005498 A1 | 5/1990 |
| WO | WO 94/20247 | 9/1994 |
| WO | WO 2004/100820 | 11/2004 |
| WO | WO2011046294 A3 | 7/2011 |
| WO | WO2014123951 A1 | 8/2014 |

* cited by examiner

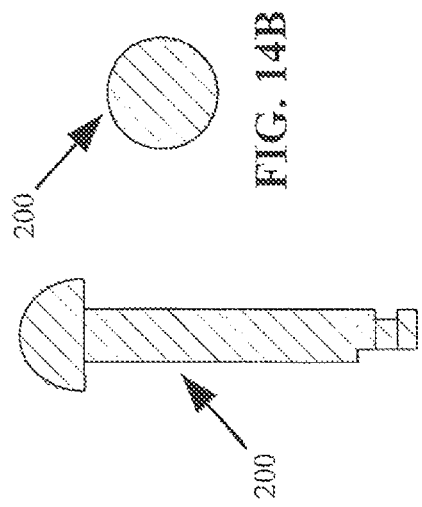
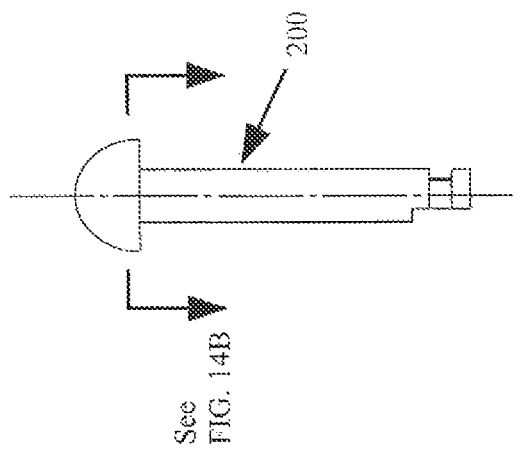
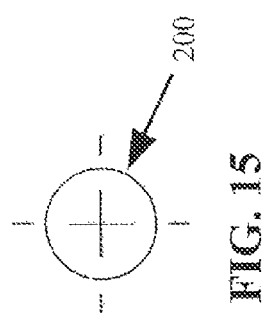
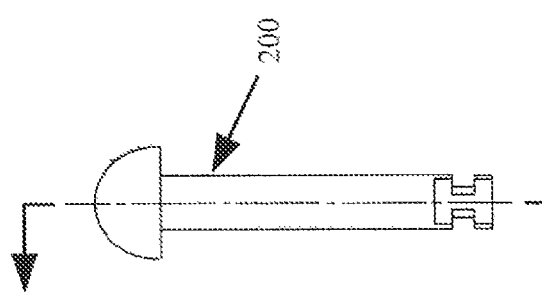
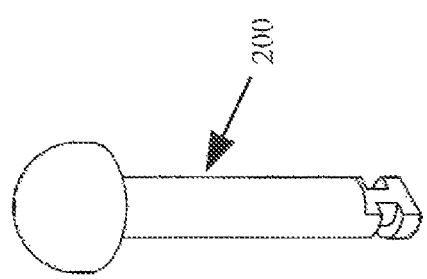

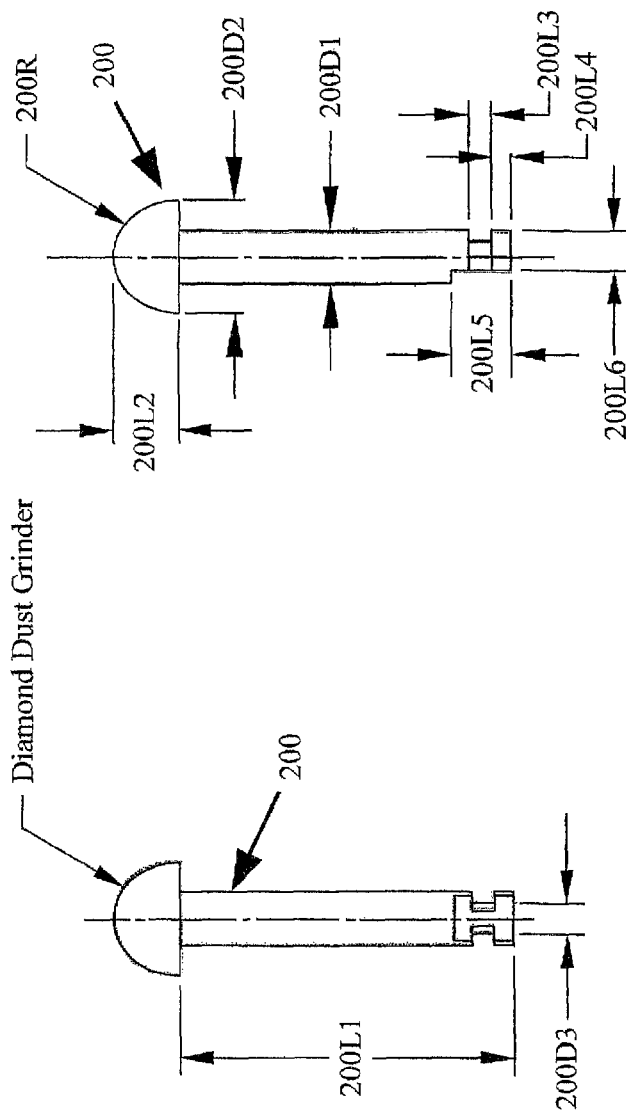

   
FIG. 18A (4 mm X 8.5 mm)  FIG. 18B (4 mm X 10 mm)  FIG. 18C (4 mm X 11.5 mm)  FIG. 18D (4 mm X 13 mm)
   
FIG. 19A (5 mm X 8.5 mm)  FIG. 19B (5 mm X 10 mm)  FIG. 19C (5 mm X 11.5 mm)  FIG. 19D (5 mm X 13 mm)
   
FIG. 20A (6 mm X 8.5 mm)  FIG. 20B (6 mm X 10 mm)  FIG. 20C (6 mm X 11.5 mm)  FIG. 20D (6 mm X 13 mm)

(6 mm X 4 mm)

(7 mm X 4 mm)

(8 mm X 4 mm)

US 12,220,296 B1

OSTEOTOMY DRILL BIT TO PRODUCE AN OPTIMALLY SHAPED JAWBONE OPENING FOR A DENTAL IMPLANT AND ABUTMENT

CROSS REFERENCES TO RELATED APPLICATIONS

This application is a continuation in part of U.S. application Ser. No. 16/704,286, filed on Dec. 5, 2019, which claims priority on U.S. Provisional Application Ser. No. 62/776,246, filed on Dec. 6, 2018, the disclosures of which are incorporated herein by reference.

FIELD OF THE INVENTION

The subject technology relates generally to preparing a surgical site for an endosseous implant, and more particularly to a dental drill bit for forming an optimally shaped opening in a human jawbone that includes a first opening portion that receives and accommodate the implant, and a second opening portion that accommodates an abutment.

BACKGROUND OF THE INVENTION

Several decades ago the loss of teeth was remedied by the use of dentures that were constructed to replace the missing teeth and which were supported by surrounding teeth and/or by underlying tissue. The use of dentures has long been supplanted by implants that receive a corresponding abutment and a crown.

Dental implants are typically endosteal, being a "root" device that is usually made of titanium, and which is inserted into a hole formed in the jaw through the bone at the alveolar ridges. During the healing period, osseointegration occurs in which the bone grows in and around the implant to provide support. Thereafter the abutment may be attached to the implant, with the abutment protruding through the periostium and being positioned to receive a crown that resembles a tooth.

There are a couple of approaches for preparing the surgical site, i.e., for creating a socket in the jaw bone region where the implant is to be installed. With either approach, a small pilot hole, usually 2 mm in diameter, is typically drilled in the alveolar ridge to define the axis of the implant socket that will ultimately receive the implant. Thereafter, with the first method, successively larger diameter osteotomes may be inserted into the pilot hole for bone compaction to widen the opening sufficiently to receive the implant. Alternatively, in the second method, the pilot hole is enlarged using a conventional dental drill bit.

The dental drill bit disclosed herein improves upon the opening formed by the prior art devices and methods.

It is noted that citing herein of any patents and published patent applications or non-patent literature is not an admission as to any of those references constituting prior art with respect to the herein disclosed dental drill bit.

OBJECTS OF THE INVENTION

It is an object of the invention to provide a dental drill bit configured to form an opening that in general will closely conform to a bullet-shaped portion of a dental implant.

It is another object of the invention to provide a dental drill bit configured to form an opening that is shaped like part of a sphere to conform to a portion of an abutment that is supported by the implant.

It is a further object of the invention to provide a dental drill bit configured to form a lower portion of an opening that closely conforms to a bullet shape of a dental implant, with an upper portion of the opening that is shaped like part of a sphere.

Further objects and advantages of the invention will become apparent from the following description and claims, and from the accompanying drawings.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Dental implants, which are usually made of titanium, are inserted or threaded into implant sockets formed in the jaw through the bone at the alveolar ridges, and serve as an anchor for prosthetic devices, such as artificial teeth and crowns. After the healing period, during which time the bone grows in and around the implant to provide support, an abutment is attached to the implant, with the abutment protruding through the periostium and being positioned to receive a crown that resembles a tooth.

Formation of the socket in the jaw bone region—an implant receiving osteotomy—typically requires drilling a pilot hole that is thereafter enlarged using one or more conventional surgical drill bits.

A dental drill bit is disclosed herein that improves upon the opening formed by the prior art devices and methods, as it produces a particularly shaped opening in a human jawbone. A first embodiment of the dental drill bit includes first, second, and third portions. The first portion includes a bullet-shaped contour formed by revolving a curve about an axis creating an apex and a bottom, and is so shaped to correspond to a bullet-shaped portion of a dental implant. The second portion includes a hemisphere frustum formed coaxial with the axis of the bullet-shaped contour, and extends from the bottom of the bullet-shaped contour, and corresponds to a portion of an abutment that is supported by the implant. The first and second portions may also each include flutes for cutting/drilling into bone. The third portion includes a shaft that extends from a bottom of the hemisphere frustum and is formed co-axial with the axis of the bullet-shaped contour, and is configured to be secured within a dental drill. A second embodiment of the drill bit is instead formed by a plurality of blades, each with an outer profile having a first portion shaped to form a bullet-shaped contour for the osteotomy, and a second portion shaped to accommodate the abutment.

A second embodiment of the dental drill bit includes: a mounting shank, and a cutting head. The mounting shank has a proximal end and a distal end, where the proximal end is configured to be received within a drill. The cutting head has a proximal end and a distal end, with the distal end of the mounting shank transitioning into the proximal end of the cutting head. The cutting head includes: four blades protruding away from an axis of the drill bit, each blade having a thickness and being positioned 90 degrees to an adjacent the blade to form a cruciform-shaped cross-section, with two pairs of the blades each positioned 180 degrees apart. Also, each of the pair of blades positioned 180 degrees apart are offset laterally a distance about equal to the blade thickness, and each blade has a shaped periphery that includes: a first radiused periphery; and a second radiused periphery. The first radiused periphery is shaped to form a hemisphere frustum-shaped socket portion when rotated about the axis of the drill bit. The second radiused periphery is shaped to form a bullet shaped socket portion when rotated about the axis of the drill bit; wherein a distal end of the first radiused periphery transitions into a proximal end of the second radiused periphery. Each blade is formed with a rake angle in a range between 5 degrees to 20 degrees. The second radiused periphery for each the pair of blades is spaced apart about 3.5 mm, and each has a length in the range of 8.5 mm to 13 mm. The distal end of the second radiused periphery is chamfered at an angle between 20 degrees to 40 degrees. In one embodiment, the second radiused periphery has a radius of about 73 mm to about 83 mm; and the first radiused periphery has a radius of about 3 mm.

BRIEF DESCRIPTION OF THE DRAWINGS

The description of the various example embodiments is explained in conjunction with appended drawings, in which:

FIG. 12 is a perspective view of a dome-shaped reamer that may be used in a finishing operation after formation of the opening in the jawbone shown in FIG. 9;

FIG. 13 is a front view of the dome-shaped reamer of FIG. 12;

FIG. 14 is a side view of the dome-shaped reamer of FIG. 12;

FIG. 14A is a cross-sectional view through the drill bit shown in FIG. 13;

FIG. 14B is a cross-sectional view through the top of the drill bit shown in FIG. 14;

FIG. 15 is a top view of the dome-shaped reamer of FIG. 12;

FIG. 16 is the front view of the dome-shaped reamer as shown in FIG. 12, but is shown dimensioned for a particular size for the dome-shaped reamer to be used after the particularly sized drill bit shown in FIG. 16-17;

FIG. 17 is a side view of the dome-shaped reamer shown in FIG. 16;

FIGS. 18A-18D illustrate a series of different sized drill bits formed as shown generally in FIGS. 1-4, with each having the same 4 mm root, but having various different lengths for the bullet portion;

FIGS. 19A-19D illustrate a series of different sized drill bits formed as shown generally in FIGS. 1-4, with each having the same 5 mm root, but having various different lengths for the bullet portion;

FIGS. 20A-20D illustrate a series of different sized drill bits formed as shown generally in FIGS. 1-4, with each having the same 6 mm root, but having various different lengths for the bullet portion;

DETAILED DESCRIPTION OF THE INVENTION

Figures 1, 2, 2A, 3, 4:
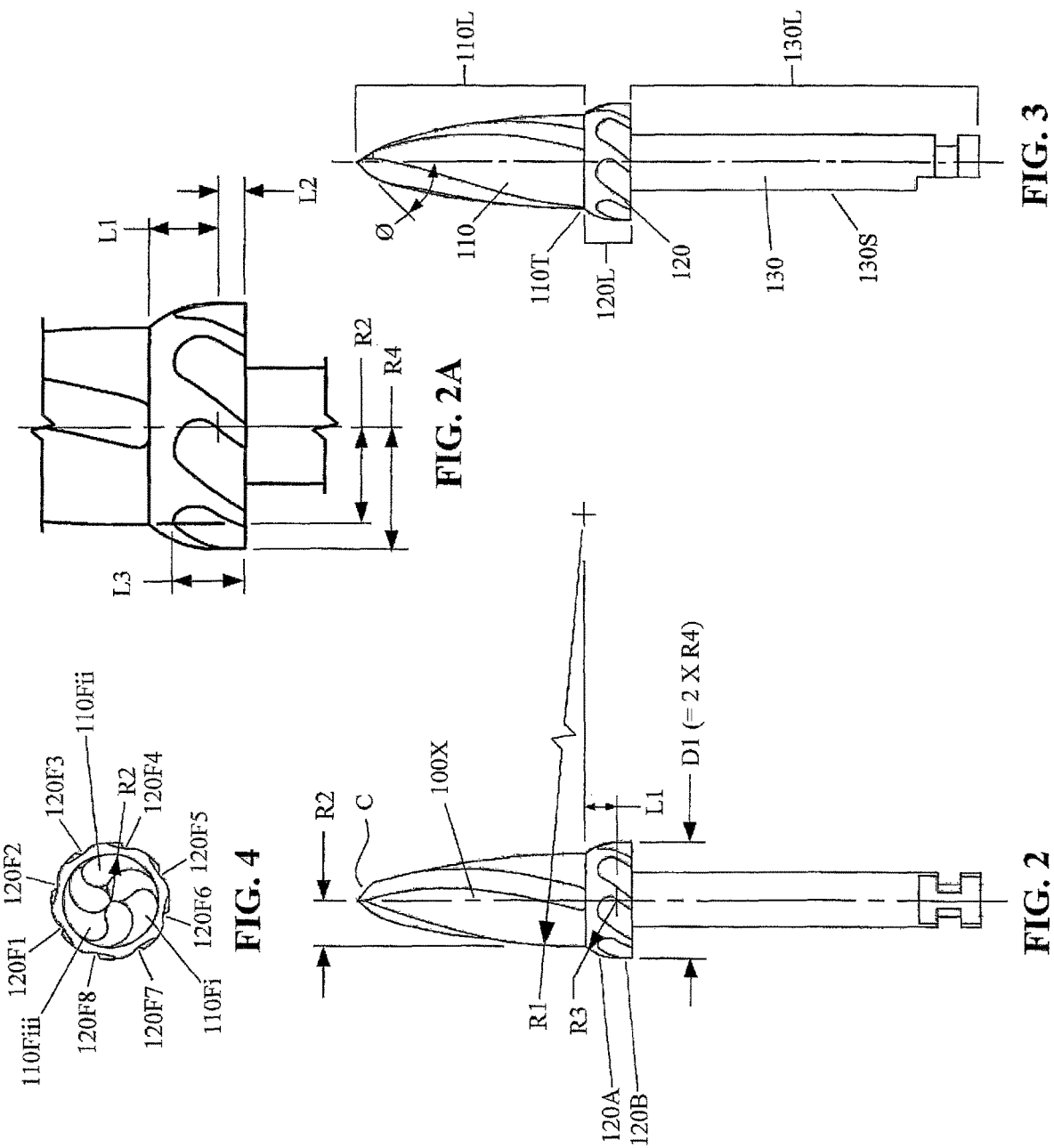
FIG. 1 is a perspective view illustrating an osteotomy drill bit in accordance with a first embodiment.
FIG. 2 is a front view of the osteotomy drill bit of FIG. 1.
FIG. 2A is an enlarged detail view of the dome portion of the osteotomy drill bit of FIG. 2.
FIG. 3 is a side view of the osteotomy drill bit of FIG. 2.
FIG. 4 is a top view of the osteotomy drill bit of FIG. 2.

As used throughout this specification, the word "may" is used in a permissive sense (i.e., meaning having the potential to), rather than a mandatory sense (i.e., meaning must), as more than one embodiment of the invention may be disclosed herein. Similarly, the words "include", "including", and "includes" mean including but not limited to.

The phrases "at least one", "one or more", and "and/or" may be open-ended expressions that are both conjunctive and disjunctive in operation. For example, each of the expressions "at least one of A, B and C", "one or more of A, B, and C", and "A, B, and/or C" herein means all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference. However, it is noted that citing herein of any patents, published patent applications, and non-patent literature is not an admission as to any of those references constituting prior art with respect to the disclosed and/or claimed apparatus/method.

Furthermore, any reference made throughout this specification to "one embodiment" or "an embodiment" means that a particular feature, structure or characteristic described in connection therewith is included in at least that one particular embodiment. Thus, the appearances of the phrases "in one embodiment" or "in an embodiment" in various places throughout this specification are not necessarily all referring to the same embodiment. Therefore, the described features, advantages, and characteristics of any particular aspect of an embodiment disclosed herein may be combined in any suitable manner with any of the other embodiments disclosed herein.

Additionally, any approximating language, as used herein throughout the specification and claims, may be applied to modify any quantitative or qualitative representation that could permissibly vary without resulting in a change in the basic function to which it is related. Accordingly, a value modified by a term such as "about" is not to be limited to the precise value specified, and may include values that differ from the specified value in accordance with applicable case law. Also, in at least some instances, a numerical difference provided by the approximating language may correspond to the precision of an instrument that may be used for measuring the value. A numerical difference provided by the approximating language may also correspond to a manufacturing tolerance associated with production of the aspect/ feature being quantified. Furthermore, a numerical difference provided by the approximating language may also correspond to an overall tolerance for the aspect/feature that may be derived from variations resulting from a stack up (i.e., the sum) of a multiplicity of such individual tolerances.

Any use of a friction fit (i.e., an interface fit) between two mating parts described herein indicates that the opening (e.g., a hole) is smaller than the part received therein (e.g., a shaft), which may be a slight interference in one embodiment in the range of 0.0001 inches to 0.0003 inches, or an interference of 0.0003 inches to 0.0007 inches in another embodiment, or an interference of 0.0007 inches to 0.0010 inches in yet another embodiment, or a combination of such ranges. Other values for the interference may also be used in different configurations (see e.g., "Press Fit Engineering and Design Calculator," available at: www.engineersedge.com/ calculators/machine-design/press-fit/press-fit-calculato-r.htm).

Any described use of a clearance fit indicates that the opening (e.g., a hole) is larger than the part received therein (e.g., a shaft), enabling the two parts to move (e.g. to slide and/or rotate) when assembled, where the gap between the opening and the part may depend upon the size of the part and the type of clearance fit—i.e., loose running, free running, easy running, close running, and sliding (e.g., for a 0.1250 inch shaft diameter the opening may be 0.1285 inches for a close running fit, and may be 0.1360 inches for a free running fit; for a 0.5000 inch diameter shaft the opening may be 0.5156 inches for a close running fit and may be 0.5312 inches for a free running fit). Other clearance amounts are used for other clearance types. See "Engineering Fit" at: https://en.wikipedia.org/wiki/Engineering_fit; and "Three General Types of Fit," available at www.mm-to.org/dclark/Reports/Encoder%20Upgrade/ fittolerences%20%5BRead-Only%5D.pdf.

It is further noted that any use herein of relative terms such as "top," "bottom," "upper," "lower," "vertical," and "horizontal" are merely intended to be descriptive for the reader, and may be based on the depiction of those features within the figures for one particular position of the device, and such terms are not intended to limit the orientation with which the device of the present invention may be utilized.

There are a couple of approaches for creating an implant socket in the jaw bone region where the dental implant is to be installed. With either approach, a small pilot hole, usually a 2 mm diameter hole, is typically drilled in the alveolar ridge to define the axis of the implant socket that will ultimately receive the implant. Thereafter, with the first method, successively larger diameter osteotomes may be inserted into the pilot hole for bone compaction to widen the opening sufficiently to receive the implant.

Figure 7:
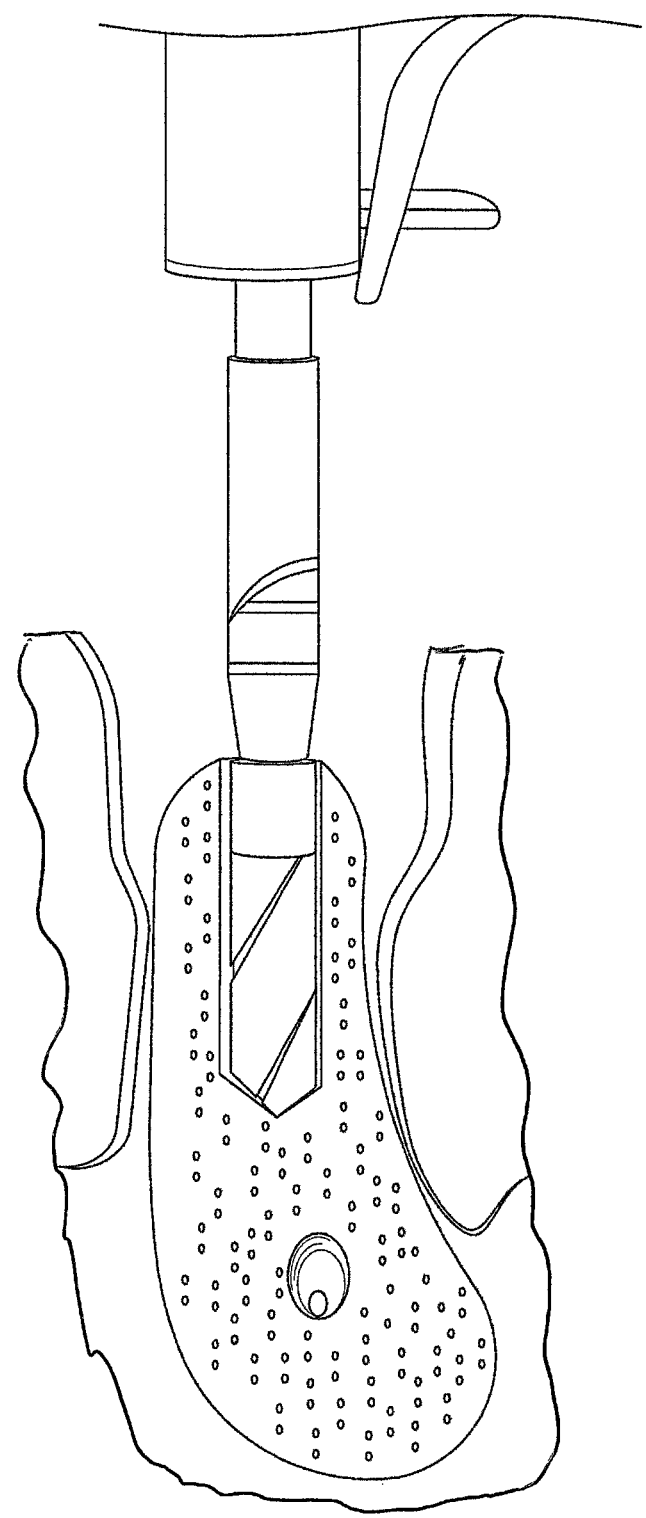
FIG. 7 is a cross-sectional image that illustrates a convention implant drill bit being used to form a cylindrical opening in the alveolar ridge for a dental implant.
Figure 8:
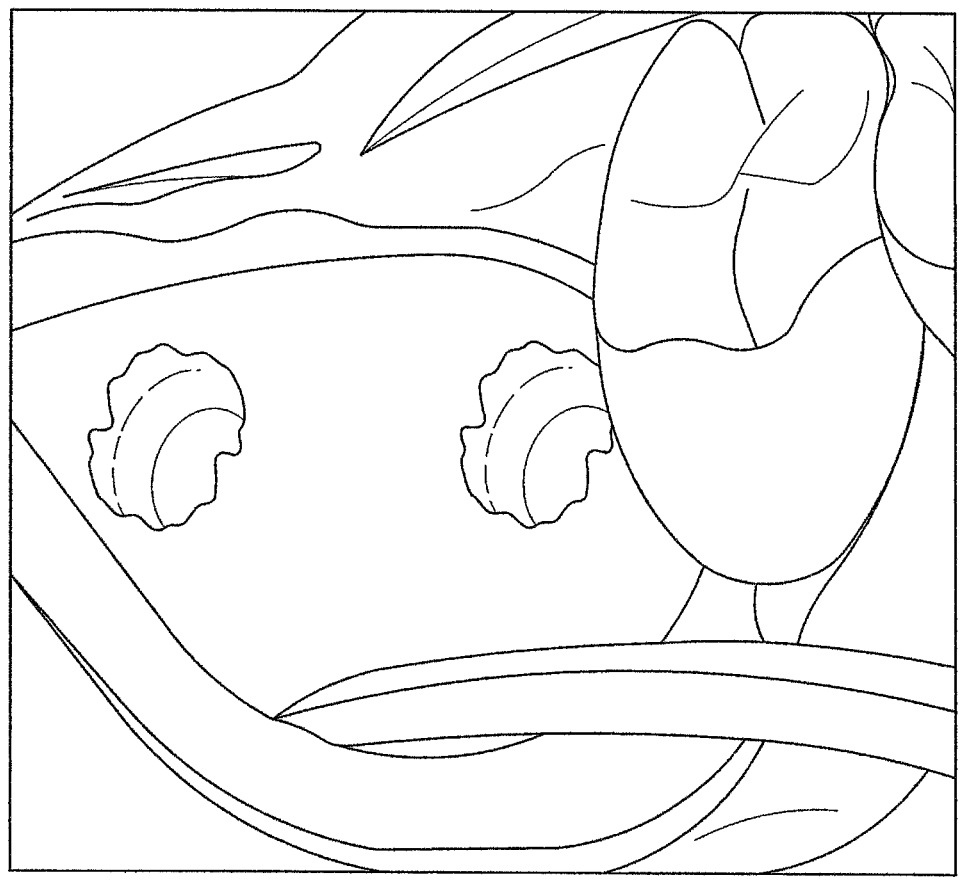
FIG. 8 is a photograph of two conventional dental implant openings formed in the jawbone of a patient using the conventional drill bit of FIG. 7.

Alternatively, in the second method, the pilot hole is enlarged using a conventional dental drill bit (see e.g., U.S. Pat. No. 5,575,650 to Niznick; U.S. Pat. No. 5,868,572 to Lazzara; and U.S. Pat. No. 5,868,572 to Kumar). FIG. 7 illustrates a conventional drill bit being used to form a cylindrical opening for a dental implant, and FIG. 8 shows a photograph of two cylindrical dental implant openings formed in the jawbone of a patient using the conventional drill bit of FIG. 7.

In accordance with at least one embodiment of the present invention, as seen in FIGS. 1-3, a dental drill bit 100 for use in a drilling machine for drilling a particularly shaped opening in a human jawbone may broadly include a first portion 110, a second portion 120, and a third portion 130.

The first portion 110 may be formed with a bullet-shaped exterior contour. In particular, the bullet-shaped contour may be formed by revolving a curve about an axis 100X, which curve may be an arc having a radius R1 that is revolved about the axis 100X. As seen in FIG. 3, the arc may have a tangency that is parallel to the axis 100X at the base of the first portion where it adjoins the second portion 120 (i.e., at 110T), and the arc may extend away from the root a certain distance 110L. As seen in FIG. 2 and FIG. 4, the revolution of the end of the arc at that tangent point 110T may form a circle having a radius R2. The bullet-shaped contour being so formed is constructed for at least a portion thereof to approximate the shape of the implant that is to be received in the socket formed using the drill bit 100. However, the bullet-shaped contour is not intended to match the exact shape of the implant. The bullet-shaped contour is sized and formed, as discussed hereinafter, to drill a hole that is corresponds to the size of the implant to be used at a particular tooth location, in particular being intended to be slightly smaller than the implant (e.g., within a range of 0.005 inches and 0.007 inches smaller diametrically in one embodiment, or within a range of 0.007 inches and 0.010 inches smaller diametrically in another embodiment, or other ranges or a combination of such ranges may be used in other embodiments), which allows the smaller sized implant to be torqued into the osteotomy made by the drill a predetermined amount. Therefore, the bullet-shaped contour is thereby sized and formed to approximate the conical shape of most implants that are currently manufactured. As discussed hereinafter, if a larger implant is to be used, the drill will need to have a larger radius R1, and similarly, smaller implants will require a smaller radius R1.

In order for the first portion 110 to be able to cut into the jaw bone, a series of flutes may be formed in the bullet-shaped contour. There are preferably three flutes-a first helical shaped flute 110Fi, a second helical shaped flute 110Fii, and a third helical shaped flute 110Fiii, each formed in the bullet-shaped contour to be equally spaced about the axis 100X, as seen in FIG. 4. The tip of the first portion 110 may also be formed to have a more distinct point, by being formed with a chamfer C that may be at an angle θ to the axis 100X. The angle θ may be in the range of 20 degrees to 60 degrees, and may more preferably be in the range of 30 degrees to 55 degrees, and may most preferably be in the range of 40 degrees to 50 degrees.

Figure 5:
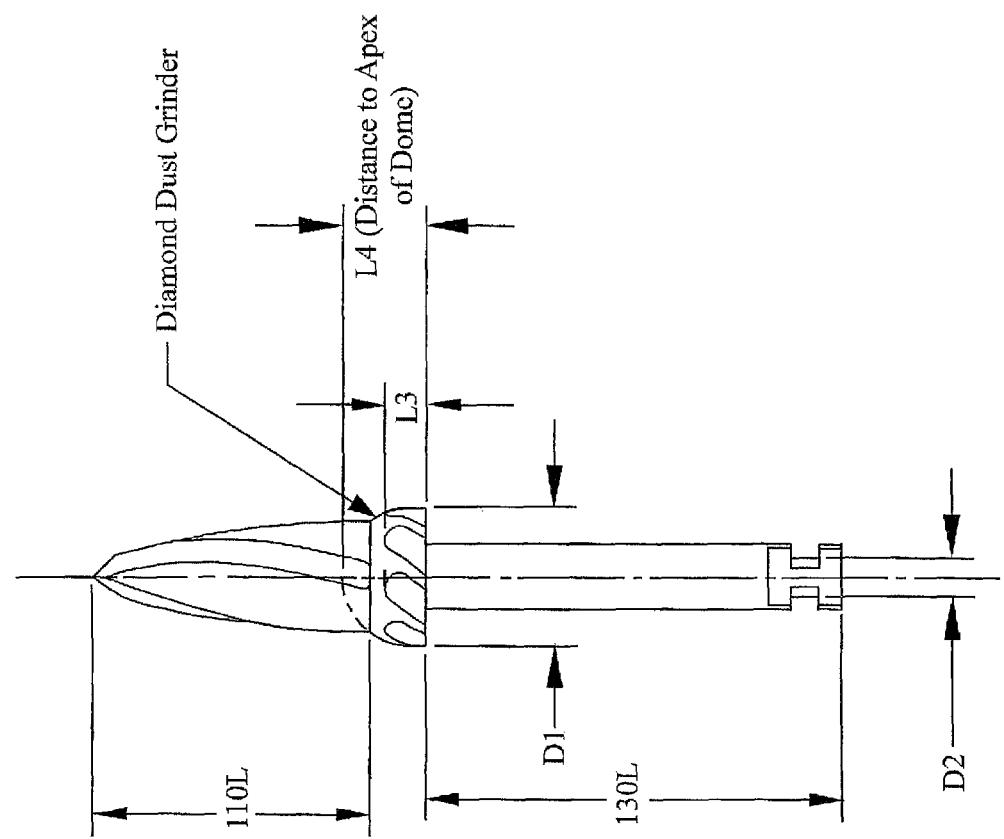
FIG. 5 is another front view of the osteotomy drill bit as shown in FIG. 1.

The second portion 120 of the dental drill bit 100, as seen in the enlarged detail view in FIG. 2A, may also have two parts (120A and 120B), where the first part 120A is formed as part of a sphere, i.e., a spherical frustum (aka, a spherical segment), and the second part 120B being a cylinder, i.e., with a diameter, D1 (FIG. 5), or radius R4 (FIG. 2A), that extends a distance L2 away from a base of the spherical frustum. Since the spherical frustum of the first part 120A preferably has a bottom that coincides with the equatorial plane of the sphere, it may also be considered to be a hemispherical frustum, having a base radius that is the full radius of the sphere, and an upper radius that is determined by the height L1 that is utilized (note that the distance to the apex of the dome, L4, as seen in FIG. 5, is simply be the sum of L1+L2). The axis of the hemispherical frustum of the first part 120A of the second portion 120 is formed to be substantially coaxial with the axis of rotation 100X used to form the bullet-shaped contour of the first portion 110. The hemispherical frustum may extend a distance L1 from the base of the bullet-shaped first portion to its equatorial plane, as seen in FIG. 2A. In one embodiment, the hemispherical frustum of the first part 120A and the cylinder of the second part 120B of the second portion 120 may also be formed with a plurality of flutes to achieved desired cutting to form the part-hemispherical surface in the alveolar ridge. The flutes may have sides that may be oriented at roughly a 45 degree angle to the axis. In one embodiment, as seen in FIG. 4, eight flutes may be formed in the hemispherical frustum of the first part 120A (i.e., flutes 120F1, 120F2, 120F3, 120F4, 120F5, 120F6, 120F7, 120F8). Other numbers of flutes may also be used. Also, in another embodiment, the flutes may be formed in the cylinder of the second part 120B of the second portion 120 and may only be formed to extend part-way along the hemispherical frustum of the first part 120A, (i.e., a distance L3) as shown in FIG. 2. In this embodiment, material removal may be accomplished by the small portion of the exposed hemispherical frustum beyond where the flutes terminate by impregnating a particular grit of diamond dust thereon (i.e., medium to coarse grit) for that surface to act as a grinder.

The hemispherical frustum of the first part 120A is so shaped with the flutes only extending a distance L3 so that it may form a corresponding opening in the bone that determines the region where the future crown and abutment will be placed, which is referred to herein as the "bedding" of the future crown and abutment, which seeks to replicate real human anatomy.

The use of the term "bedding" refers to the anatomically correct receiving zone for the future crown and abutment. Current drills only make the osteotomy for the implant. They fail to drill a shallow zone immediately outside of the implant that will function as the site to receive and be shaped to correspond to the future abutment and crown. Drill 100 is conceived and configured to accomplish both. Therefore, the "bedding" may be considered to be a second osteotomy, or an extension of the existing osteotomy that functions to accommodate the abutment, which abutments all tend to have a spherically shaped portion. Therefore, the corresponding spherical surface that is formed in the bone by the hemispherical frustum creates an anatomically correct spherical surface portion (a proper "receiving zone") for the future abutment (and crown) that will be placed 3-4 months later.

The third portion 130 may include a shaft 130S having a diameter D3, that may extend from the end of the cylinder of the second part 120B of the second portion 120. The axis of the shaft 130S is formed to be substantially co-axial with the axis of rotation 100X used to form the bullet-shaped contour of the first portion 110, and may extend a distance 130L from the end of the cylinder of the second part 120B, as seen in FIG. 3. A portion of the distal end of the shaft 130S may be formed with an annular recess having a diameter, D2, and length, L5 (FIG. 6), being positioned a distance, L6, away from the end of the shaft 130S, and which may also be notched to form a flat surface thereon (i.e., having a notch length, L7, from the end of the shaft, and a depth that reduces the full shaft dimeter to have a maximum extent of L8), which features on the shaft may be used for securing the dental drill bit 100 in the chuck of a drill machine.

Figure 9:
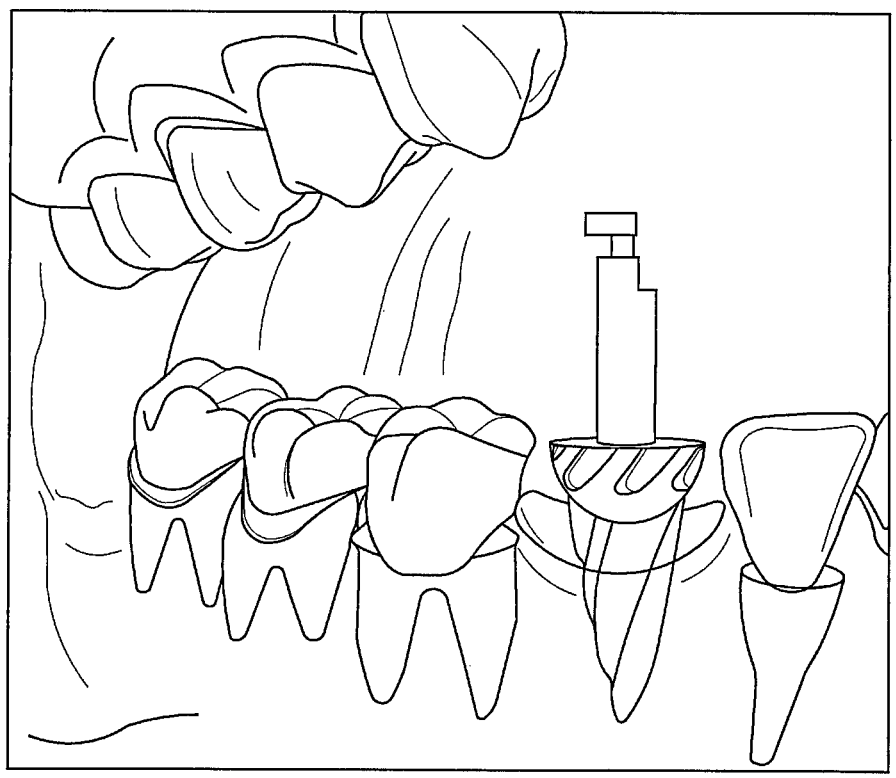
FIG. 9 illustrates a first embodiment of the dental drill bit disclosed herein being used to form an optimally shaped opening in a human jawbone.
Figure 10:
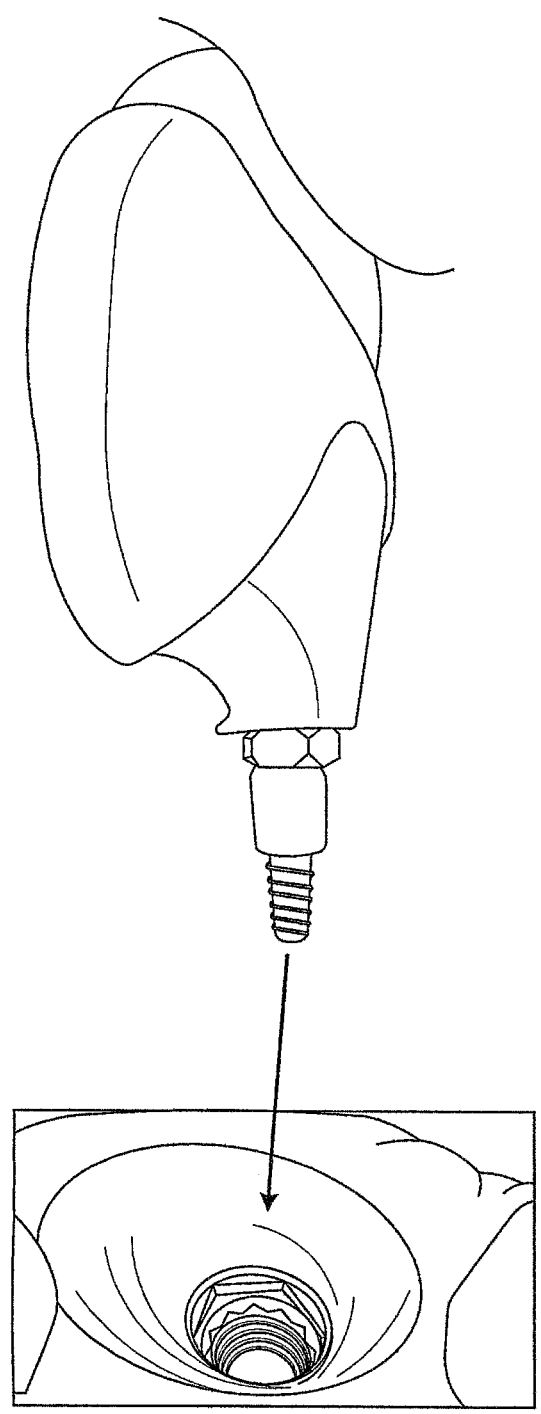
FIG. 10 is an exploded view that illustrates the opening in the jawbone that was formed in FIG. 9, but after an implant has been received therein, and prior to installation of the abutment and crown shown therein.
Figure 11:
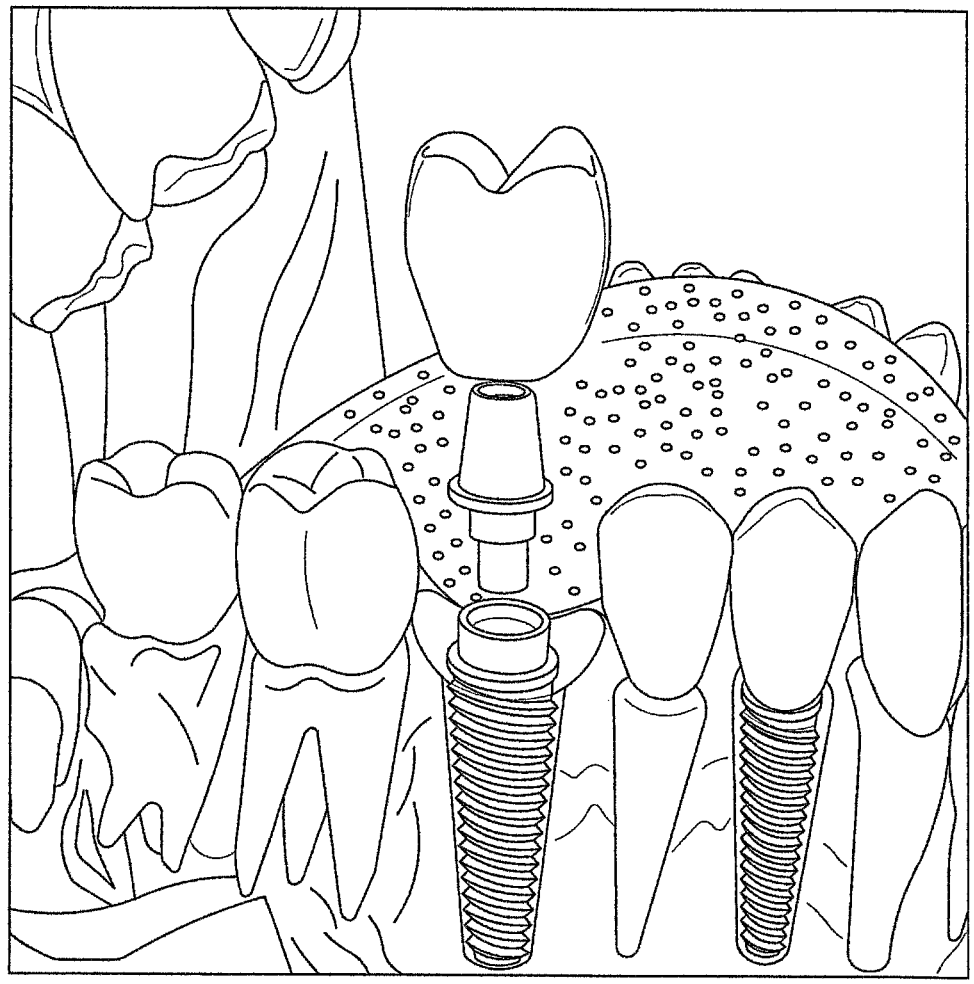
FIG. 11 is a transparent view showing an implant after being received in an opening formed as shown in FIG. 9, and just prior to receiving the abutment and crown thereon.

After the dental drill bit 100 has been used to form the two part opening in the jawbone (see FIG. 9) by using both the bullet-shaped exterior contour of the first portion 110 and the hemispherical frustum of the first part 120A of the second portion 120, the dome-shaped reamer 200 shown in FIGS. 12-14 may be used to clean up the spherical surface of the exposed jawbone. The spherical surface of the dome-shaped reamer 200 may be impregnated with a fine grit of diamond dust for the surface to act as a finish grinder.

Figure 6:
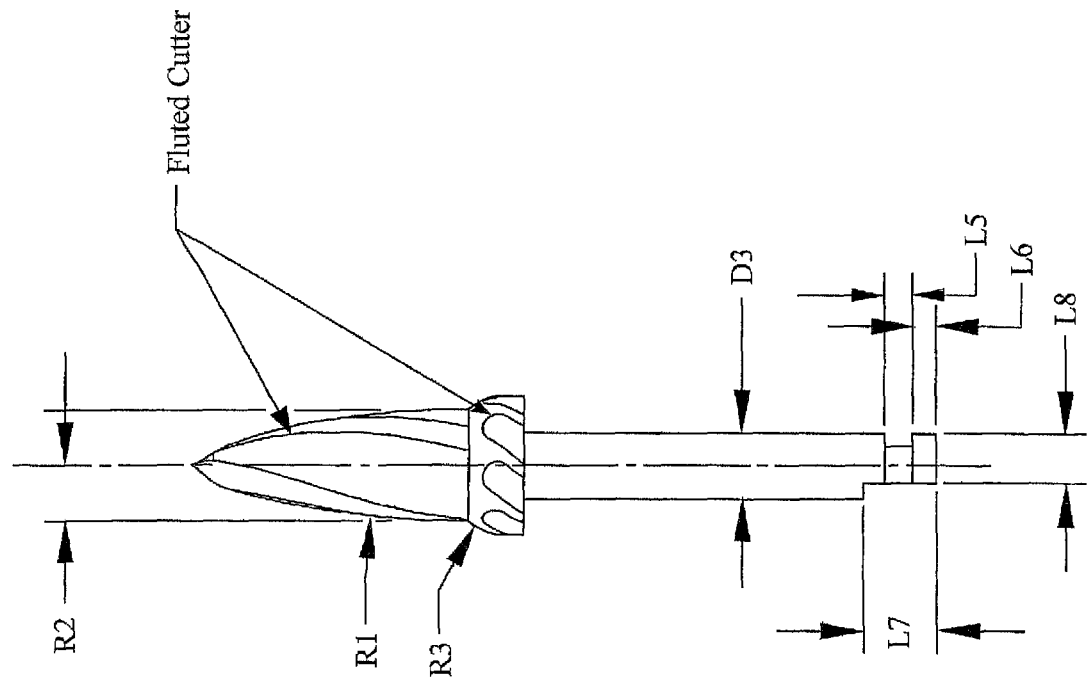
FIG. 6 is a side view of the drill bit shown in FIG. 5.

FIGS. 5-6 illustrates one size for the dental drill bit, in which the radius R1 of the arc is 34.6 mm, and the arc is positioned to revolve about the axis 100X at a radius R2 of 2 mm (i.e., a 4 mm diameter) to form a length 110L of 10 mm, and where the radius R3 of the hemispherical frustum of the first part 120A of the second portion 120 is 2.5 mm (D1=5 mm), and the length L3 is 1.5 mm and length L4 is 3 mm, making the length L1 1.5 mm. The shaft and notch dimension may be: D2=1.4, D3=2.35, L5=1 mm, L6=0.85 mm, L7=2.65, and L8=1.78 mm. (Note, the corresponding finish reamer 200 is shown dimensioned in FIGS. 16-17, and would have the following parameters: 200L1=15 mm, 200L2=3 mm, 200L3=1 mm, 200L4=0.85 mm, 200L5=2.65 mm, 200L6=1.78 mm, 200D1=2.35 mm, 200D2=5 mm, 200D3=1.4 mm, and 200R1=2.5 mm). This particular size drill bit that is shown in FIGS. 5-6 is also shown in FIG. 18B (i.e., having a 4 mm diameter or 2 mm radius, and a 10 mm length for the bullet portion). FIGS. 18A-18D illustrate a family of such drill bits each of which has the 4 mm diameter and a different length 110L (i.e., lengths of 8.5 mm, 10 mm, 11.5 mm, and 13 mm). Similarly, FIGS. 19A-19D illustrate a family of such drill bits each of which has a 5 mm diameter, and a varying length, and FIGS. 20A-20D illustrate a family of such drill bits each of which has a 6 mm diameter and a varying length.

Figure 21A:
FIGS. 21A-21C illustrate a series of different sized dome-shaped reamers formed as shown generally in FIGS. 13-15.
Figure 21B:
Figure 21C:

FIGS. 21A-21C show a corresponding series of finish reamers.

It is noted that the 34.58 mm radius and the corresponding radius R2 of 2 mm that is used for the dental drill bit of FIGS. 5-6 is used to accommodate implants that are 4 mm in diameter, which implant size is the most common diameter used in implant dentistry. It should also be noted that it is difficult to specifically identify which sized drill bit would tend to be used for each of the tooth numbers 2-18 and 15-31 because of the variation in bone sizes between different patients. The size of the implant that will be placed in the socket, and therefore the drill bit size used at a particular site, will to be selected to fit the width and the length of the bone at the tooth number undergoing the surgery, for that particular patient (i.e., the size/quality of the bone at tooth number 15 for a 5 foot tall 150 pound elderly and edentulous man will likely be quite different than the size/quality of the bone at tooth number 15 for a 6' 6" tall 275 pound 25 year old professional football player). In general, smaller implants will require socket formation using a smaller diameter drill bit, while larger implants will require use of larger diameter drill bits. As such, a kit may be formed containing each of the drill bits shown in FIGS. 18A-21C, and may include multiple drill bits of various diameters and lengths. The kit permits a drill bit to be chosen according to the dental implant surgeon's assessment of the bone parameters of the particular patient (e.g., width, length, bone quality, etc.). The drill bit that is selected for a particular tooth number of a particular patient is intended to be undersized relative to the implant that is to be used. After the osteotomy is drilled, the softness of the bone will allow the user to place the implant, similar to where an undersized hole is drilled into a wood beam into which a wood screw with a larger diameter is torqued and secured. The softness of the bone (or wood) relative to the implant (or screw) permits it to be installed despite the relative size difference.

It is further noted that the radius R1 and the radius of revolution R2 are interrelated, and as one radius changes in moving from a first drill bit size to a second drill bit size, so does the other radius; thus, the radius of 34.58 is not used on each drill bit shown in FIGS. 18A-20D.

Figure 22:
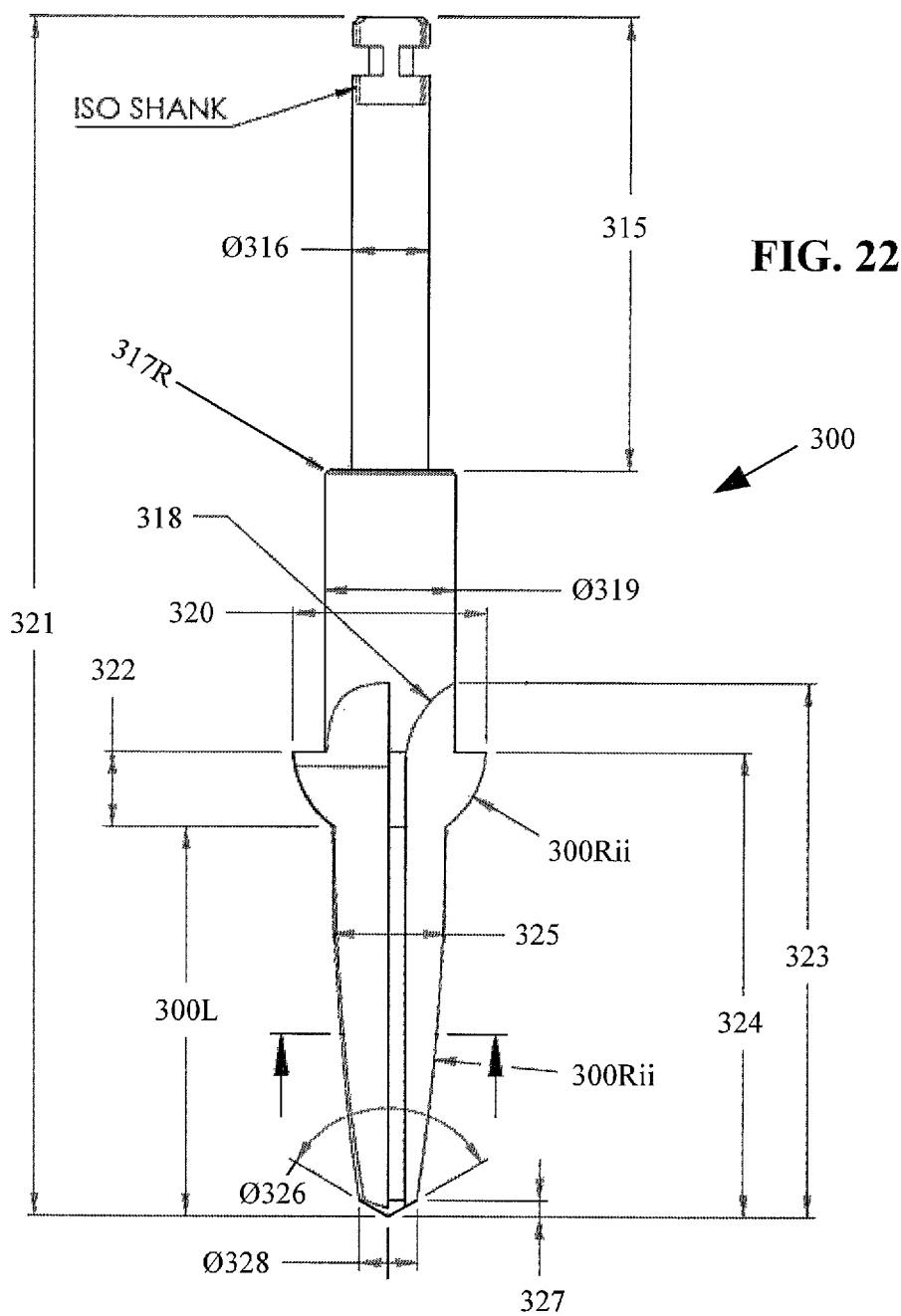
FIG. 22 is a front view of another embodiment of an osteotomy drill bit.
Figure 23:
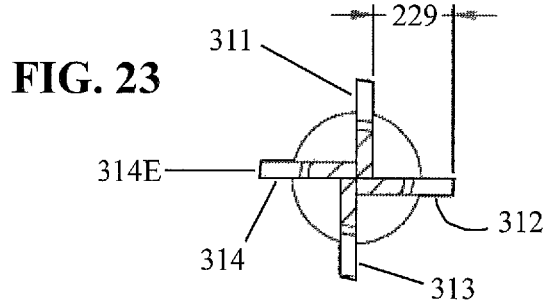
FIG. 23 is a cross-sectional view through the tip of the osteotomy drill bit of FIG. 22.

A drill bit 300 is shown in FIGS. 22-23, and is particularly shaped to form a bullet-shaped osteotomy that will receive an implant platform, and to accomplish scalloping of the bone at the same time by also forming an opening that is shaped like part of a sphere to conform to a portion of an abutment that is supported by the implant platform.

Figure 22A:
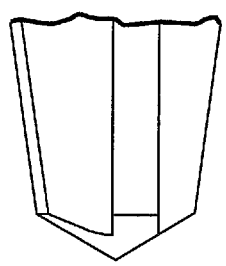
FIG. 22A is an enlarged detail view of the tip of the osteotomy drill bit of FIG. 22.
Figure 22B:
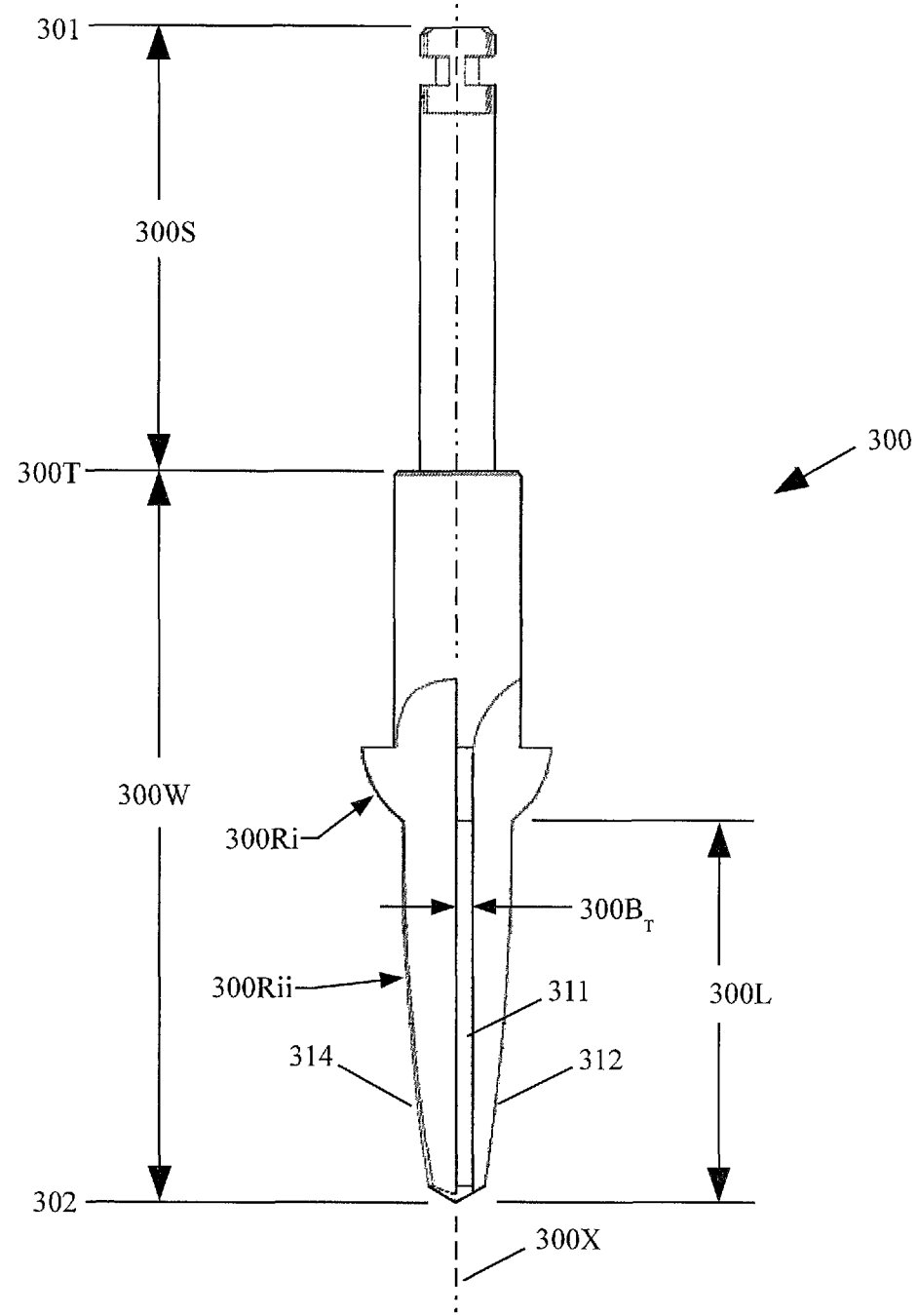
FIG. 22B is the front view of FIG. 22, but which annotates additional features of the osteotomy drill bit shown therein.
Figure 24:
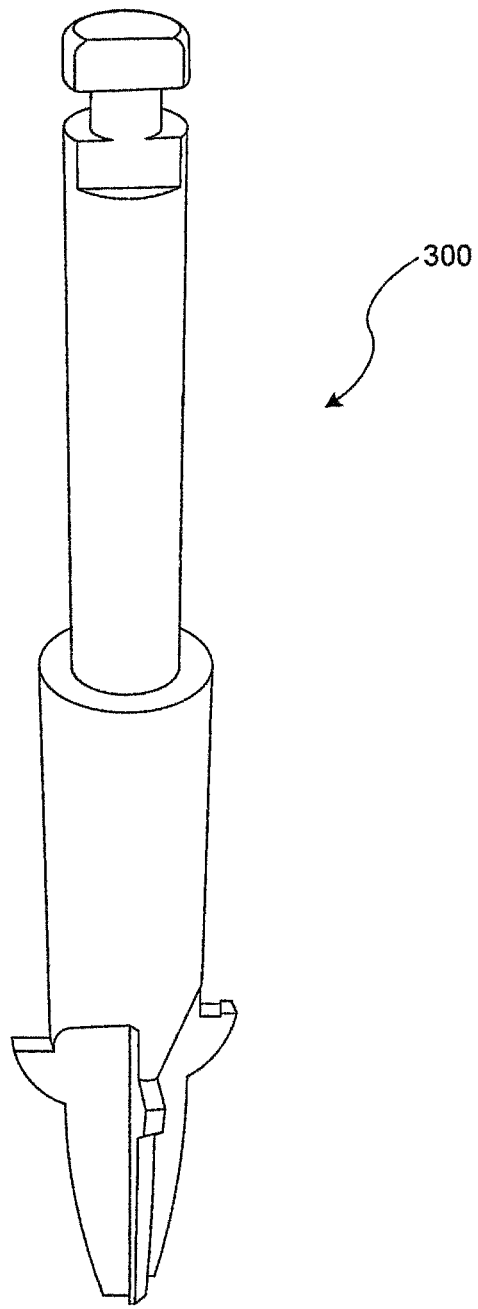
FIG. 24 is a perspective view of the osteotomy drill bit of FIG. 22.

As seen in FIG. 22B, the drill bit 300 may extend from a first end 301 to a second end 302, and may include a mounting shank 300S, having a portion proximate to the first end 301 configured to be received in a chuck of a dental drill or hand piece. The drill bit 300 may also have a working portion 300W that is adapted to cut or remove bone and/or tissue.

The distal end of the mounting shank 300S may transition into the proximal end of the cutting head 300W at 300T. The cutting head incudes four blades protruding away from an axis 300X of the drill bit, a first blade 311, a second blade 312, a third blade 313, a fourth blade 314. Each of the blades have a thickness $300B_T$ and each blade is positioned 90 degrees to an adjacent blade, as seen in FIG. 23, to form a cruciform-shaped cross-section, with two pairs of the blades (i.e., blade pair 311/313, and blade pair 312/314), where the two blades in each pair are positioned 180 degrees apart (i.e., the sharp distally protruding edge of blade 311 is 180 degrees with respect to blade 313). The rake angle at the distal end of each blade (e.g., end 314E shown in FIG. 23) may be in the range of about five degrees to about twenty degrees. Each of the pairs of blades that are positioned 180 degrees apart are also offset laterally a distance that is about equal to the blade thickness, as shown in FIG. 23. Each blade has a shaped periphery that includes: a first radiused periphery 300Ri; and a second radiused periphery 300Rii, where a distal end of the first radiused periphery transitions into a proximal end of the second radiused periphery, as seen in FIGS. 22 and 22B. The first radiused periphery 300Ri is shaped to form a hemisphere frustum-shaped socket portion when rotated about the 300X of the drill bit. The second radiused periphery 300Rii is shaped to form a bullet shaped socket portion when rotated about the axis 300X of the drill bit. To be suitable for most implant sockets that may need to be formed, the second radiused periphery 300Rii preferably has a radius in the range of about 73 mm to about 83 mm, which radii for each pair of blades are spaced apart about 3.5 mm (see FIG. 22), and which may have various different lengths 300L depending upon which tooth location it will be used at to form the osteotomy, e.g., 8.5 mm, 10 mm, 11.5 mm, and 13 mm. The first radiused periphery may have a radius of about 3 mm. A distal end of the second radiused periphery 300Rii is preferably chamfered at an angle between 20 degrees to 40 degrees, and more preferably chamfered at an angle of between 25 degrees to 35 degrees, to form the tip shown in FIG. 22A.

The drill bit 300 shown in FIG. 22 may, in one embodiment, be formed to the following dimensions to be usable at one or more particular locations:

300L=12 mm
300Ri=3 mm
300Rii=77.95
315=14 mm
θ316=2.34±0.01 mm
317R=0.10×45 degrees
318R=3 mm (max)
θ319=4 mm
$320=6^{+0.02/-0.05}$ mm
321=37 mm
322=2.30 mm
323=16.44
324=14.30
325=3.50±0.03
θ326=120 degrees
327=0.52
θ328=1.80±0.03
329=2.50 (×4)

While illustrative implementations of one or more embodiments of the present invention are provided hereinabove, those skilled in the art and having the benefit of the present disclosure will appreciate that further embodiments may be implemented with various changes within the scope of the present invention. Other modifications, substitutions, omissions and changes may be made in the design, size, materials used or proportions, operating conditions, assembly sequence, or arrangement or positioning of elements and members of the exemplary embodiments without departing from the spirit of this invention.

Accordingly, the breadth and scope of the present disclosure should not be limited by any of the above-described example embodiments, but should be defined only in accordance with the following claims and their equivalents.

What is claimed is:

1. A dental drill bit configured to drill a particularly shaped opening in a tooth and in a portion of a human jawbone, the drilled opening being particularly shaped to receive a dental implant screw and a portion of an abutment therein, said dental drill bit comprising:
    a mounting shank, said mounting shank having a proximal end and a distal end, said proximal end configured to be received within a drill;
    a cutting head, said cutting head having a proximal end and a distal end, said proximal end of said cutting head transitioning into said distal end of said mounting shank; said cutting head comprising: four blades protruding away from an axis of said drill bit, each blade of said four blades having a thickness and being positioned 90 degrees to an adjacent blade of said four blades to form a cruciform-shaped cross-section; and each blade of said four blades having a shaped periphery comprising:
    a first radiused periphery, and
    a second radiused periphery;
    wherein said first radiused periphery comprises: an arc being a portion of a circle configured to form a spherical frustum-shaped socket portion, when rotated about the axis of said drill bit, being defined by a first plane and a second plane, with the spherical frustum-shaped socket portion thereby formed being shaped to match a portion of a spherical surface of the abutment, wherein the tangent at a proximal end of said arc is parallel to said axis of said dental drill bit;
    wherein said second radiused periphery comprises:
    an arc being a portion of a circle and having a first end being coextensive with, and perpendicular to, said second plane;
    wherein a radius of said arc of said second radiused periphery is greater than a distance between said first end of said arc of said second radiused periphery and the axis of said dental drill bit; and wherein said second radiused periphery is thereby configured to form a bullet shaped socket portion, when rotated about said axis of said drill bit, to match at least a portion of a shape of the dental implant screw;

wherein a proximal end of said second radiused periphery transitions into a distal end of said first radiused periphery and is positioned a distance away from said axis of said dental drill bit to form a desired root radius;

wherein the tangent at said proximal end of said second radiused periphery is parallel to said axis of said dental drill bit; and wherein a distal end of said second radiused periphery is chamfered to truncate a length of each of said four blades to reduce a length of the bullet shaped socket portion formed therewith to correspond to a length of the dental implant screw.

2. The dental drill bit according to claim 1, wherein said four blades are formed into two pairs, with each pair of said two pairs of said four blades being positioned 180 degrees apart and being offset laterally from the axis a distance about equal to one-half of said thickness.

3. The dental drill bit according to claim 2, wherein each blade of said four blades is formed with a rake angle being in a range between 5 degrees to 20 degrees.

4. The dental drill bit according to claim 3, wherein said distal end of said second radiused periphery is chamfered at an angle between 20 degrees to 40 degrees.

5. The dental drill bit according to claim 4, wherein said second radiused periphery has a radius of about 73 mm to about 83 mm.

6. The dental drill bit according to claim 5, wherein said first radiused periphery has a radius of about 3 mm.

7. The dental drill bit according to claim 1, wherein said first plane is co-planar with the equatorial plane of the sphere.

* * * * *